United States Patent [19]

Taniguchi et al.

[11] Patent Number: 4,514,555
[45] Date of Patent: Apr. 30, 1985

[54] PROCESS FOR THE PRODUCTION OF HIGH MOLECULAR WEIGHT ORGANOALUMINUM POLYMERS

[75] Inventors: Isoji Taniguchi, Kyoto; Yoshiharu Kimura, Ohmihachiman, both of Japan

[73] Assignee: Idemitsu Kosan Company Limited, Tokyo, Japan

[21] Appl. No.: 586,074

[22] Filed: Mar. 5, 1984

[30] Foreign Application Priority Data

Apr. 16, 1983 [JP] Japan .................................. 58-67564
Sep. 2, 1983 [JP] Japan .................................. 58-162321
Nov. 2, 1983 [JP] Japan .................................. 58-206815

[51] Int. Cl.$^3$ ............................................. C08G 79/10
[52] U.S. Cl. ........................................ 528/9; 528/166; 528/271; 528/361; 528/395
[58] Field of Search .................... 528/9, 271, 166, 361, 528/395

[56] References Cited

U.S. PATENT DOCUMENTS 2,744,074 5/1956 Theobald .................................. 528/9
2,844,551 7/1958 Orthner et al. ...................... 528/271
4,069,236 1/1978 Hutchison et al. .................. 528/395

FOREIGN PATENT DOCUMENTS 541843 6/1957 Canada ................................. 528/395
783679 9/1957 United Kingdom ................ 528/395

Primary Examiner—Harold D. Anderson
Attorney, Agent, or Firm—Frishauf, Holtz, Goodman & Woodward

[57] ABSTRACT

A process for producing a high molecular weight organoaluminum polymer by using an organoaluminum compound, water and an organic acid.

The organoaluminum polymer obtained herein is suitable for preparing fibers.

13 Claims, No Drawings

PROCESS FOR THE PRODUCTION OF HIGH MOLECULAR WEIGHT ORGANOALUMINUM POLYMERS

BACKGROUND OF THE INVENTION

Materials of high strength and super heat resistance have recently been desired in various industrial fields. Among such materials are alumina fibers which are suitable for use in fabrication of composite materials in combination with metals, ceramics and so forth.

A method of calcining fiber precursors made of organoaluminum polymers has received increasing attention for the production of superior alumina fibers. However, a method has not been developed yet which enables to produce with ease and further with high efficiency high molecular weight organoaluminum polymers which are suitable for use in production of such fiber precursors. That is, although it is known that organoaluminum polymers can be prepared by reacting organoaluminum compounds with water, high molecular weight organoaluminum polymers suitable for use in preparing, e.g., fibers are difficult to produce by conventional procedures.

SUMMARY OF THE INVENTION

An object of the present invention is to provide a process for efficiently producing high molecular weight organoaluminum polymers suitable for use in preparing, e.g., fibers.

The present invention relates to a process for producing a high molecular weight organoaluminum polymer by reacting an organoaluminum compound with water, which process is characterized in that as reactants an organoaluminum compound represented by the general formula (I):

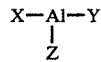

(wherein X, Y and Z are each a hydrogen atom, an alkyl group, an alkoxyl group, or an acyloxyl group, provided that when any one of X, Y and Z is an acyloxyl group, at least one of the others is an acyloxyl group) is used, and an organic acid is used in an amount such that the total amount of the organic acid and the acyloxyl group contained in the organoaluminum compound is from 1.1 to 11 moles per mole of the organoaluminum compound.

DETAILED DESCRIPTION OF THE INVENTION

The organoaluminum compounds as used herein, as described above, have the general formula (I):

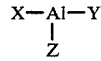

In the general formula (I), X, Y and Z are each a hydrogen atom, an alkyl group, an alkoxyl group, or an acyloxyl group, provided that when any one of X, Y and Z is an acyloxyl group, at least one of the other is an acyloxyl group.

The alkyl group represented by X, Y and Z includes a methyl group, an ethyl group, a n-propyl group, an isopropyl group, a n-butyl group and its isomers (e.g., an isobutyl group, a sec-butyl group, and a tert-butyl group), a n-pentyl group and its isomers, and a n-hexyl group and its isomers.

The alkoxyl group includes a methoxyl group, an ethoxyl group, a n-propoxyl group, an iso-propoxyl group, a n-butoxyl group and its isomers, a n-pentoxyl group and its isomers, and a n-hexanoxyl group and its isomers.

X, Y and Z also each represent an acyloxyl group. In this case, at least two of X, Y and Z should be acyloxyl groups. For example, the compounds in which Y and Z are acyloxyl groups are represented by the general formula (II):

and the compounds in which all of X, Y and Z are acyloxyl groups are represented by the general formula (III):

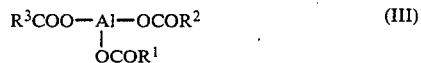

In addition, the compounds in which all of X, Y and Z are alkoxyl groups are represented by the general formula (IV):

In the general formulae (II), (III) and (IV), $R^1$, $R^2$ and $R^3$ may be the same or different and each represent at least one organic radical. Furthermore, any two of $R^1$, $R^2$ and $R^3$ may be the same, the remaining one being different. The organic radical includes a saturated or unsaturated aliphatic substituent, an alicyclic substituent, and an aromatic substituent.

Specifically the saturated aliphatic substituent includes a methyl group, an ethyl group, a n-propyl group, an isopropyl group, a n-butyl group and its isomers, a n-pentyl group and its isomers, and a n-nonyl group and its isomers.

The alicyclic substituent includes a cyclohexyl group.

The unsaturated aliphatic substituent includes an alkenyl group (e.g., a vinyl group, an allyl group, and a crotyl group), an unsaturated, mono-, di-, tri- or like, hydrocarbon group (e.g., a butadienyl group and an octatrienyl group), and an alkinyl group (e.g., an ethinyl group and a propinyl group).

The aromatic substituent includes various aryl groups such as a phenyl group, a tolyl group, an anisyl group, and a naphthyl group.

The saturated aliphatic substituent, unsaturated aliphatic substituent, alicyclic substituent, and aromatic substituent may contain at least one radical, such as a chlorine atom, an amino group, a hydroxyl group, a carboxyl group, an alkoxyl group, and an aryl group.

In the process of the present invention, a mixture of two or more organoaluminum compounds in which $R^1$, $R^2$ and $R^3$ are different can be used.

In accordance with the process of the present invention, organic acids are added in the reaction of the organoaluminum compounds represented by the formula (I) and water. Most of the known organic acids can be used in the present invention. Suitable examples are saturated or unsaturated aliphatic monocarboxylic acids (excluding formic acid), alicyclic carboxylic acids, aromatic monocarboxylic acids, dicarboxylic acids, hydroxycarboxylic acids, and their derivatives containing a substituent or substituents in the main chain thereof.

Typical examples of the saturated aliphatic monocarboxylic acids are acetic acid, propionic acid, butyric acid, isobutyric acid, pivalic acid, octanoic acid, lauric acid, and stearic acid.

Typical examples of the unsaturated aliphatic monocarboxylic acids are acrylic acid, methacrylic acid, crotonic acid, and oleic acid.

A typical example of the alicyclic carboxylic acids is cyclohexanecarboxylic acid.

Typical examples of the aromatic monocarboxylic acids are succinic acid, glutaric acid, phthalic acid, and cyclohexanedicarboxylic acids.

Typical examples of the hydroxycarboxylic acids are glycolic acid, lactic acid, and mandelic acid.

Typical examples of the substituents of the above-described carboxylic acid derivatives are a chlorine atom, an amino group, a hydroxyl group, a carboxyl group, an alkoxyl group, a phenyl group, and an aryl group.

When the organoaluminum compound having acyloxyl groups as represented by the formula (II) or (III) is used, the type of the organic acid to be added in the reaction of the organoaluminum compound and water is preferably determined as follows:

It is considered that amongst the organic radicals contained in the organoaluminum compound (i.e., $R^1$ and $R^2$, or $R^1$, $R^2$ and $R^3$) those radicals producing the corresponding acids ($R^1COOH$, $R^2COOH$, or $R^3COOH$) having the highest acidity remain in the final high molecular weight organoaluminum polymers. It is therefore preferred that organic acids identical to those corresponding to the organic radicals of the organoaluminum compound used herein or organic acids higher in acidity than those to be used.

For example, when the organic radicals of the organoaluminum compound to be used in the reaction are a propionyl group and an undecyl group, since the corresponding organic acids are propionic acid and lauric acid, it is preferred that propionic acid of higher acidity or organic acids having an acidity higher than that of propionic acid be used as the organic acids. Typical examples of these organic acids include hexanoic acid, butyric acid, valeric acid, acetic acid, methacrylic acid, and acrylic acid. Although typical organic acids of the saturated or unsaturated aliphatic monocarboxylic acids are listed above, the present invention is not limited thereto.

In the present invention, the above-described organic acids may be used singly or in combination with each other.

In the practice of the present invention, the organoaluminum compound, water, and organic acid may be used as such or without use of any solvents. In general, however, it is preferred for them to be diluted with suitable organic solvents for convenience of handling and also for effective condensation polymerization. In particular, when solid acids are used as the organic acids, they are preferably used after dilution with organic solvents.

Any organic solvents can be used as long as they are capable of dissolving the organoaluminum compounds, water, and organic acids and, furthermore, do not react therewith. Typical examples are hydrocarbon solvents such as benzene, toluene, xylene, tetralin, decalin, pentane, hexane, and heptane, ether solvents such as dioxane, diethyl ether, 1,2-dimethoxyethane, tetrahydrofuran, and anisol, tert-amine solvents such as pyridine, picoline, and triethylamine, and polar solvents such as dimethylsulfoxide and dimethylformamide.

In the condensation polymerization reaction of the organoaluminum compound and water, water may be added at once but it is preferred to gradually add dropwise. It is also convenient for handling that water is used in the form of solutions with suitable organic solvents. In the case of the organic acids, they may be added at once but it is preferred for them to gradually add dropwise as in the case of water.

The order in which the organoaluminum compound, water, and organic acid are added is not critical in the process of the present invention, but it is convenient to determine the order in which water and the organic acid are added to the organoaluminum compound.

With regard to the order of addition of the organic acid, it may be added in the course of the condensation polymerization between the organoaluminum compound and water, or after the condensation polymerization, or water may be added after the organic acid is added to the organoaluminum compound.

Furthermore, the following procedures (i), (ii) may be employed; (i) part of the organic acid is added in the course of the condensation polymerization between the organoaluminum compound and water, and then the remaining organic acid is added after completion of the condensation polymerization, (ii) the organic acid is added to the polymer formed by the condensation polymerization.

With regard to the amount of the organic acid to be added in the process of the present invention, the organic acid is added in an amount such that the total amount of the organic acid and the acyloxy group contained in the organoaluminum compound is from 1.1 to 11 moles per mole of the organoaluminum compound. If the organic acid is added within the range as defined above, there can be formed organoaluminum polymers which have an increased molecular weight and thus are suitable for use in production of fibers. If the amount of the organic acid added is too small, an increase in the molecular weight of the organoaluminum polymer due to the addition of the organic acid cannot almost be expected. On the other hand, even if the organic acid is added excessively, the molecular weight of the organoaluminum polymer is scarcely increased.

The amount of the organic acid being added is determined based on the total amount of the organic acid and the acyloxyl group contained in the organoaluminum compound. Thus, when an organoaluminum compound not containing an acyloxyl group is used, the organic acid is added in an amount of from 1.1 to 11 moles, preferably from 1.4 to 3.5 moles per mole of the organoaluminum compound. In a case where the organoaluminum compound contains two acyloxyl groups as in the above-described general formula (II), the amount of the organic acid being added is determined as described above, and the organic acid itself is sufficient to be added in an amount ranging between 0.2 and 9 moles, preferably between 0.5 and 2.5 moles per mole of the organoaluminum compound. In a case where the organoaluminum compound contains three acyloxyl groups as in the formula (III), the amount of the organic acid being added is also determined as described above, and the organic acid itself is sufficient to be added in an amount of from 0.2 to 8 moles, preferably from 0.5 to 2.5 moles per mole of the organoaluminum compound.

The amount of water to be used in the condensation polymerization of the organoaluminum compound is not critical and can be determined appropriately. Usually it is effective for the production of high molecular weight organoaluminum polymers that water be used in an amount of from 1.0 to 3.5 moles per mole of the organoaluminum compound. Especially preferred is the range of from 1.0 to 2.0 moles per mole of the organoaluminum compound. If the amount of water added is too small, there cannot be formed high molecular weight organoaluminum polymers. On the other hand, if the amount of water added is too large, the condensation polymerization reaction is accelerated, resulting in the formation of organoaluminum polymers which are excessively polymerized and cross-linked and thus are insoluble in water. However, when at least one of X, Y and Z in the formula (I) represents an alkoxyl group, water can be added in an amount of less than 1.0 mole per mole of the organoaluminum compound, since water is formed in the condensation polymerization reaction.

The reaction temperature in the process of the present invention is not critical as long as it is not more than 200° C. Preferably the reaction temperature is chosen depending on the type of the organoaluminum compound, organic acid, or organic solvent. In commercial practice of the present invention, it is economical for the condensation polymerization reaction to be performed at a temperature ranging between about 0° and 60° C.

The organoaluminum polymers produced by the process of the present invention have a reduced viscosity of from 0.4 to 5.5 (solvent: a mixed solvent of equal weights of tetrachloroethane and phenol; temperature: 30° C.; concentration: 0.5 grams per deciliter); that is, they are high molecular weight polymers suitable for spinning and so forth.

On the other hand, in accordance with conventional methods even if the amount of water added is from 1.0 to 1.2 moles per mole of trialkyl aluminum such as triethyl aluminum, there can be formed only low molecular weight organoaluminum polymers having a reduced viscosity of 0.2 or less.

The present invention is described in greater detail with reference to the following examples, although the present invention is not limited thereto.

EXAMPLE 1

In a 200-milliliter three necked flask equipped with a dropping funnel, a reflux condenser, and a three-way cock was placed 6.66 grams (58 millimoles) of triethylaluminum, which was then diluted with 24 milliliters of tetrahydrofuran. The solution thus prepared was maintained at −30° C. in an argon atmosphere, and 10 milliliters of a tetrahydrofuran solution containing 1.04 grams (58 millimoles) of distilled water was slowly added dropwise while stirring with a magnetic stirrer for one hour. After completion of addition, the resulting mixture was heated to raise the temperature to room temperature. Then, 10.3 grams (87 millimoles) of 3-ethoxypropionic acid was added. The mixture thus prepared was allowed to stand overnight at room temperature to be converted into a uniform, clear and viscous solution.

This solution showed good stringiness at room temperature, said stringiness being a measure of fiber molding.

The solution was then poured into 500 milliliters of hexane and reprecipitated to yield 10.8 grams of a white organoaluminum polymer in a powder form. The reduced viscosity of the polymer as determined in a mixed solvent of equal weights of phenol and tetrahydrofuran (concentration: 0.5 gram per deciliter; temperature: 30° C.) was 0.81.

EXAMPLE 2

In the same atmosphere and apparatus as used in Example 1, 7.35 grams (50 millimoles) of diisobutylaluminum hydride was diluted with 30 milliliters of dioxane, and 30 milliliters of a solution of 17.7 grams (150 millimoles) of 3-ethoxypropionic acid in dioxane was added dropwise and reacted at −78° C.

The reaction mixture was gradually heated to raise the temperature to 50° C. Then, 10 milliliters of a solution of 1 gram (56 millimoles) of distilled water in dioxane was added and reacted overnight while fully stirring. The reaction mixture was then poured into a large amount of hexane and reprecipitated to yield 12.8 grams of an organoaluminum polymer.

The reduced viscosity of the polymer as determined under the same conditions as in Example 1 was 0.52.

EXAMPLE 3

In the same atmosphere and apparatus as used in Example 1, 5.45 grams (25 millimoles) of diisopropoxyaluminum sec-butoxide was diluted with 20 milliliters of decalin, and 0.45 gram (25 millimoles) of distilled water was slowly added dropwise at 150° C. while fully stirring. At this temperature, they were reacted for 7.5 hours while stirring. Then, 5.6 milliliters (75 millimoles) of propionic acid was added, and the mixture was stirred at 150° C. for additional 7.5 hours.

After being cooled, the reaction mixture was poured into a large amount of hexane and reprecipitated to yield 4.74 grams of an organoaluminum polymer.

The reduced viscosity of the polymer in a mixed solvent of equal weights of phenol and tetrachloroethane (concentration: 0.5 gram per deciliter; temperature: 30° C.) was 3.7.

EXAMPLE 4

In the same atmosphere and apparatus as used in Example 1, 5.9 grams (31 millimoles) of diethylaluminum 3-methylphenolate (b.p., 130° C. at 0.1 millimeter mercury (°C./0.1 mmHg)) was dissolved in 20 milliliters of tetrahydrofuran, and 10 milliliters of a solution of 1.1 grams (62 millimoles) of distilled water in tetrahydrofuran was gradually added dropwise and reacted at room temperature while fully stirring. After the addition was completed, the mixture was stirred for 2 hours. The tetrahydrofuran was distilled off under reduced pressure, yielding about 6.2 grams of a white product in a flake form. To 1 gram of the product were added 10 milliliters of toluene and 2 milliliters of 3-methoxypropionic acid, and the resulting mixture was stirred at room temperature.

The reaction mixture was allowed to stand for one day and night, and then poured into a large amount of hexane and reprecipitated to yield 2.1 grams of a white organoaluminum polymer in a powder form.

The reduced viscosity of the polymer in a mixed solvent of equal weights of phenol and tetrachloroethane (concentration: 0.4 gram per deciliter; temperature: 30° C.) was 1.2. The reduced viscosity of a condensation polymerization product of diethylaluminum 3-methylphenolate and water as produced under the same conditions as above and as determined in the same solvent as above was 0.03.

EXAMPLE 5

In the same atmosphere and apparatus as used in Example 1, 9.9 grams (50 millimoles) of triisobutyl aluminum was diluted with 40 milliliters of toluene, and 20 milliliters of a solution of 15 grams (75 millimoles) of lauric acid in tetrahydrofuran was added dropwise at room temperature while fully stirring. Subsequently, under the same temperature as in Example 6, 1.8 grams (100 millimoles) of distilled water was added dropwise and stirred for 2 hours.

Then, 22.8 grams (150 millimoles) of para-anisic acid was further added, and the resulting mixture was stirred at room temperature for one day and night. The reaction mixture was poured into a large amount of hexane and reprecipitated to yield 15.1 grams of an organoaluminum polymer.

The reduced viscosity of the polymer in dimethylformamide (concentration: 0.5 gram per deciliter; temperature: 30° C.) was 3.4.

EXAMPLE 6

In the same atmosphere and apparatus as used in Example 1, 10.2 grams (50 millimoles) of aluminum triisopropoxide was diluted with 30 milliliters of benzene, and 13.5 grams (75 millimoles) of distilled water was added at room temperature while fully stirring. In the course of the addition, 20 milliliters of a solution of 9.6 grams (75 millimoles) of cyclohexanecarboxylic acid in benzene was added. The mixture was then stirred at 50° C. for 12 hours. At the end of the time, the reaction mixture was poured into a large amount of hexane and reprecipitated to yield 10.6 grams of an organoaluminum polymer.

The reduced viscosity of the polymer in a mixed solvent of equal weights of phenol and tetrahydrofuran (concentration: 0.5 gram per deciliter; temperature: 30° C.) was 0.76.

EXAMPLE 7

In a 200-milliliter three necked flask equipped with a dropping funnel, a reflux condenser, and a three way cock was placed 5.45 grams (25 millimoles) of diisopropoxyaluminum sec-butoxide, which was then diluted with 20 milliliters of decalin. The solution thus prepared was maintained at 150° C. in an argon atmosphere, and 0.45 gram (25 millimoles) of distilled water was slowly added dropwise while stirring with a magnetic stirrer. They were reacted at 150° C. for 7.5 hours while stirring. Then, a prescribed amount of propionic acid was added, and the resulting mixture was stirred at 50° C. for additional 7.5 hours.

After being cooled, the reaction mixture was poured into a large amount of hexane and reprecipitated to obtain organoaluminum polymers.

The reduced viscosity of the polymers in a mixed solvent of equal weights of phenol and tetrachloroethane (concentration: 0.4 gram per deciliter; temperature: 30° C.) was determined. The results obtained are shown in Table 1.

TABLE 1

| Run | [PA]/[AMD]*[1] | Yield (gram) | $\eta sp/c$*[2] |
| --- | --- | --- | --- |
| 1 | 1.5 | 3.69 | 1.99 |
| 2 | 2.0 | 4.63 | 2.22 |
| 3 | 2.5 | 4.68 | 0.67 |
| 4 | 3.0 | 4.78 | 0.77 |

*[1]Molar ratio of propionic acid (PA) to diisopropoxy-aluminum sec-butoxide (AMD).
*[2]Reduced viscosity determined in a mixed solvent of equal weight of phenol and tetrachloroethane (concentration: 0.4 gram per deciliter; temperature: 30° C.)

EXAMPLE 8

In the same atmosphere and apparatus as used in Example 7, 1.02 grams (50 millimoles) of aluminum triisopropoxide was diluted with 30 milliliters of benzene, and 1.35 grams (75 millimoles) of distilled water was added dropwise and reacted at room temperature for 3 hours while fully stirring. Then, 14.42 grams (100 millimoles) of n-capric acid was added, and the resulting mixture was allowed to stand at room temperature for one day and night.

The reaction mixture was concentrated to dryness under reduced pressure and then washed with a large amount of hexane, yielding 12.3 grams of an organoaluminum polymer.

The reduced viscosity of the polymer in a mixed solvent of equal weights of phenol and tetrachloroethane (concentration: 0.5 gram per deciliter; temperature: 30° C.) was 2.1.

EXAMPLE 9

In the same atmosphere and apparatus as used in Example 7, 7.65 grams (25 millimoles) of aluminum triphenoxide was diluted with 30 milliliters of toluene. While moderately refluxing the toluene, 0.9 gram (50 millimoles) of distilled water was added, and they were reacted for 3 hours.

Subsequently, 11.8 grams (100 millimoles) of 3-ethoxypropionic acid was added and reacted for 5 hours under the same conditions as above.

After being cooled, the reaction mixture was poured into a large amount of hexane and reprecipitated to yield 4.8 grams of a polymer.

The reduced viscosity of the polymer in a mixed solvent of equal weights of phenol and tetrachloroethane (concentration: 0.5 gram per deciliter; temperature: 30° C.) was 0.41. This polymer can be spinned, yielding good fibers.

EXAMPLE 10

A mixture of 50 millimoles of ethylaluminum di-3-ethoxypropionate, which had been prepared from a molecular equivalent of triethylaluminum and two molecular equivalents of 3-ethoxypropionic acid, and 50 milliliters of toluene was placed in a three-necked flask equipped with a dropping funnel, a reflux condenser, and a three-way cock, and 10 milliliters of a 1,4-dioxane solution containing 0.9 gram (50 millimoles) of distilled water and 1.18 grams (10 millimoles) of 3-ethoxypropionic acid were added dropwise and reacted at room temperature in a nitrogen atmosphere while stirring with a a magnetic stirrer. In several hours, there was formed a uniform, clear and viscous solution. This solution showed a good stringiness, which was a measure of fiber-forming properties. The solution was poured into 500 milliliters of hexane and reprecipitated to yield 12.7 grams of a white organoaluminum polymer in a powder form.

The reduced viscosity of the polymer in a mixed solvent of equal weights of phenol and tetrachloroethane (concentration: 0.5 gram per deciliter; temperature: 30° C.) was 0.76.

EXAMPLE 11

To the viscous solution obtained in Example 10 was added 2.95 grams (25 millimoles) of 3-ethoxypropionic acid, and the resulting mixture was allowed to stand overnight at room temperature. The mixture became more viscous than before the addition of the acid. Thereafter, reprecipitation was carried out in the same manner as in Example 10 to yield 13.1 grams of an organoaluminum polymer.

The reduced viscosity of the polymer in the same solvent and under the same conditions as in Example 10 was 0.98.

EXAMPLE 12

A mixture of 11.5 grams (50 milliliters) of isobutylaluminum dipropionate, which had been prepared by reacting a molecular equivalent of triisobutyl aluminum and two molecular equivalents of propionic acid, and 50 milliliters of tetrahydrofuran was placed in the same apparatus as used in Example 10, and 0.9 gram (50 millimoles) of water and 20 milliliters of a tetrahydrofuran solution containing 3.7 grams (50 millimoles) of propionic acid were added dropwise and reacted at 50° C. while stirring. On maintaining the reaction mixture at 50° C. for several hours, it became a viscous solution. The solution was poured into a large amount of hexane and reprecipitated to yield 11.4 grams of a white organoaluminum polymer in a powder form.

The reduced viscosity of the polymer in the same solvent and under the same conditions as in Example 10 was 1.8.

EXAMPLE 13

A mixture of 24.2 grams (50 millimoles) of isopropoxyaluminum dilaurate, which had been prepared by reacting a molecular equivalent of aluminum isopropoxide and two molecular equivalents of lauric acid, and 100 milliliters of benzene was placed in the same apparatus as used in Example 10, and 1.1 grams (60 millimoles) of water was added dropwise and reacted at 80° C. in a nitrogen atmosphere. Then, 5 grams (25 millimoles) of lauric acid was added, and the resulting mixture was stirred at 80° C. for several hours and was further allows to stand at room temperature for one day and night. The mixture became a uniform, viscous solution. The benzene was distilled off under reduced pressure, and the residue was washed with hexane and dried, yielding 21 grams of a white organoaluminum polymer in a resin form.

The reduced viscosity of the polymer in benzene (concentration: 0.5 gram per deciliter; temperature: 30° C.) was 5.05.

EXAMPLE 14

A mixture of 13.7 grams (50 millimoles) of isobutyl aluminum monopropionate mono-3-ethoxypropionate, which had been prepared by reacting a molecular equivalent of triisobutyl aluminum and a molecular equivalent of 3-ethoxypropionic acid, and 30 milliliters of tetrahydrofuran was placed in the same apparatus as used in Example 10, and 1.8 grams (100 millimoles) of water and 50 milliliters of a tetrahydrofuran solution containing 7.4 grams (100 millimoles) of propionic acid were added dropwise while stirring at room temperature. Then the mixture was stirred at room temperature for 10 hours to yield a viscous solution. This viscous solution was poured into a large amount of hexane and reprecipitated to obtain 10.5 grams of an organoaluminum polymer.

The reduced viscosity of the polymer in the same solvent and under the same conditions as in Example 10 was 1.3.

EXAMPLE 15

A mixture of 22.8 grams (50 millimoles) of aluminum tricaprate, which had been prepared by reacting a molecular equivalent of ethylaluminum diisopropoxide and three molecular equivalents of capric acid, and 100 milliliters of toluene was placed in the same apparatus as used in Example 10, and 28.8 grams (100 millimoles) of capric acid was further added at 100° C. in a nitrogen atmosphere while stirring. After 1 hour, 10 milliliters of a dioxane solution containing 0.9 gram (50 millimoles) of water was added dropwise, and the resulting mixture was stirred at the same temperature as above for 3 hours. There was formed a uniform, viscous solution. The toluene was distilled off under reduced pressure and the residue was washed with ethanol and dried, yielding 20.5 grams of a while organoaluminum polymer in a rubber form.

The reduced viscosity of the polymer in toluene (concentration: 0.5 gram per deciliter; temperature: 30° C.) was 0.69.

EXAMPLE 16

In a 300-milliliter four necked flask equipped with a dropping funnel, a stirrer, a thermometer, and a reflux condenser was placed 90 milliliters (50 moles) of distilled water, which was then maintained at 75° C. While vigorously stirring, 10 grams (0.05 mole) of aluminum triisopropoxide was added dropwise. Simultaneously with the addition of the aluminum tetrapropoxide, a white precipitate was formed. This precipitate was filtered off immediately after the completion of the addition and transferred to a flask equipped with a reflux condenser. Then, 50 grams (0.68 mole) of propionic acid and 100 milliliters of toluene were added, and the resulting mixture was refluxed in a stream of nitrogen at 140° C., removing the water formed by azeotropy. The precipitate was gradually dissolved. In 15 hours, the reaction mixture became almost homogeneous. It was then refluxed for additional 10 hours. At the end of the time, the reaction was stopped, and the product was poured into a large amount of hexane, isolated by reprecipitation, and then dried.

The product had the same infrared absorption spectrum and nuclear magnetic resonance spectrum as those of the product as obtained in Example 7; the product was found to be identical to the organoaluminum polymer of Example 7. The yield of the product was 14.3 grams, and its reduced viscosity in a mixed solvent of equal weights of phenol and tetrachloroethane (concentration: 0.5 gram per deciliter; temperature: 30° C.) was 0.85.

What is claimed is:

1. A process for producing a high molecular weight organoaluminum polymer comprising reacting an organoaluminum compound with water, the improvement wherein the reactants are (1) water, (2) an organoaluminum compound represented by the general formula (I):

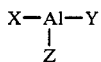

wherein X, Y and Z are each a hydrogen atom, an alkyl group, an alkoxyl group, or an acyloxyl group, provided that when any one of X, Y and Z is an acyloxyl group, at least one of the others is an acyloxyl group and (3) an organic acid in an amount such that the total amount of the organic acid and the acyloxyl group contained in the organoaluminum compound is from 1.1 to 11 moles per mole of the organoaluminum compound.

2. The process as claimed in claim 1, wherein the molar ratio of the water to the organoaluminum compound is from 1:1 to 3:5:1.

3. The process as claimed in claim 1, wherein the organic acid is added during the reaction of the organoaluminum compound and water.

4. The process as claimed in claim 1, wherein the organic acid is added prior to the reaction of the organoaluminum compound and water.

5. The process as claimed in claim 1, wherein the organic acid is added after the reaction of the organoaluminum compound and water.

6. The process as claimed in claim 1, wherein a part of the organic acid is added during the reaction of the organoaluminum compound and water, and the remainder is added after completion of the reaction.

7. The process as claimed in claim 1, wherein when the organoaluminum compound is represented by the general formula (II):

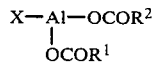

wherein X is as defined above, and $R^1$ and $R^2$ are the same or different and are each at least one organic radical, the organic acid is added in an amount of from 0.2 to 9 moles per mole of the organoaluminum compound.

8. The process as claimed in claim 1, wherein when the organoaluminum compound is represented by the general formula (III):

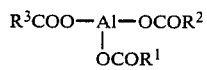

wherein X is as defined above, and $R^1$, $R^2$ and $R^3$ are the same or different and are each at least one organic radical, the organic acid is added in an amount of from 0.2 to 8 moles per mole of the organoaluminum compound.

9. The process as claimed in claim 1, wherein the organoaluminum compound is represented by the general formula (IV):

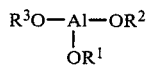

wherein $R^1$, $R^2$ and $R^3$ are the same or different and are at least one organic radical.

10. The process as claimed in claim 2, wherein the organic acid is added during the reaction of the organoaluminum compound and water.

11. The process as claimed in claim 2, wherein the organic acid is added prior to the reaction of the organoaluminum compound and water.

12. The process as claimed in claim 2, wherein the organic acid is added after the reaction of the organoaluminum compound and water.

13. The process as claimed in claim 2, wherein a part of the organic acid is added during the reaction of the organoaluminum compound and water, and the remainder is added after completion of the reaction.

* * * * *